US008553955B2

(12) United States Patent
Arakita et al.

(10) Patent No.: US 8,553,955 B2
(45) Date of Patent: Oct. 8, 2013

(54) IMAGE PROCESSING APPARATUS, X-RAY COMPUTED TOMOGRAPHY APPARATUS, AND IMAGE PROCESSING METHOD

(75) Inventors: Kazumasa Arakita, Nasushiobara (JP); Yoshihiro Ikeda, Sakura (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 188 days.

(21) Appl. No.: 13/004,097

(22) Filed: Jan. 11, 2011

(65) Prior Publication Data

US 2011/0170658 A1 Jul. 14, 2011

(30) Foreign Application Priority Data

Jan. 14, 2010 (JP) .................................. 2010-006110

(51) Int. Cl.
*G06K 9/00* (2006.01)
(52) U.S. Cl.
USPC ............ 382/128; 382/131; 382/132; 382/107

(58) Field of Classification Search
USPC .................................................. 382/128, 131
See application file for complete search history.

(56) References Cited

U.S. PATENT DOCUMENTS

| 7,623,679 | B2 * | 11/2009 | West et al. ..................... 382/103 |
| 8,317,705 | B2 * | 11/2012 | Stapf et al. ..................... 600/443 |
| 2003/0100832 | A1 * | 5/2003 | Criton et al. .................. 600/443 |
| 2009/0022379 | A1 * | 1/2009 | Tashiro et al. ................. 382/131 |
| 2009/0080779 | A1 * | 3/2009 | Chefd'hotel et al. ......... 382/209 |

* cited by examiner

*Primary Examiner* — Tom Y Lu
(74) *Attorney, Agent, or Firm* — Yoshida & Associates, LLC

(57) ABSTRACT

According to one embodiment, an image processing apparatus comprises a storage unit configured to store a plurality of volume data acquired by imaging a predetermined part of an object, the plurality of volume data corresponding to a plurality of phases, a calculation unit configured to calculate a spatial motion vector of each voxel included in each volume data by performing registration between the plurality of volume data, an image generation unit configured to generate an image representing a local motion of the diagnosis part using the motion vector of each voxel, and a display unit configured to display the image representing the local motion of the diagnosis part.

18 Claims, 10 Drawing Sheets

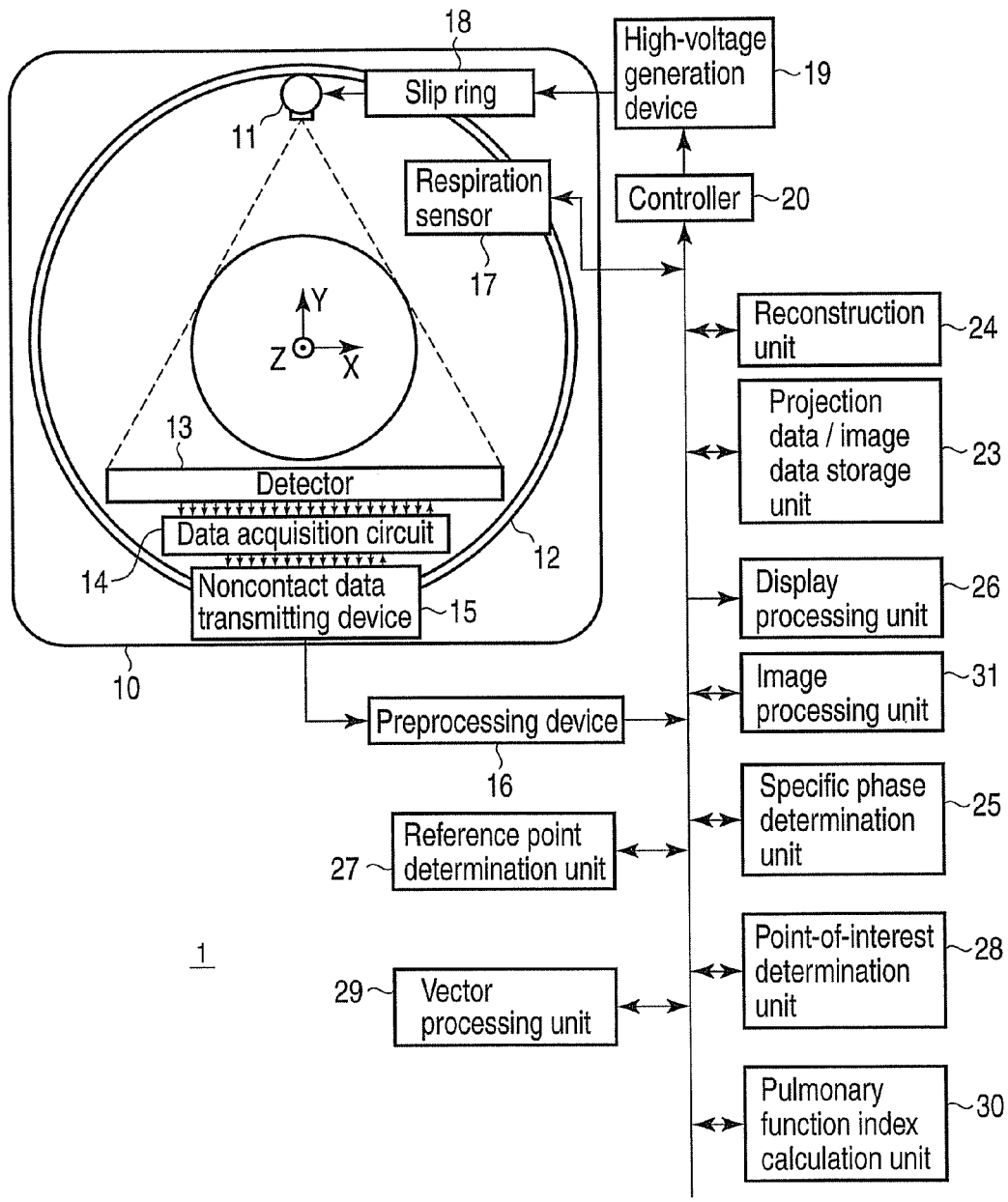
F I G. 1

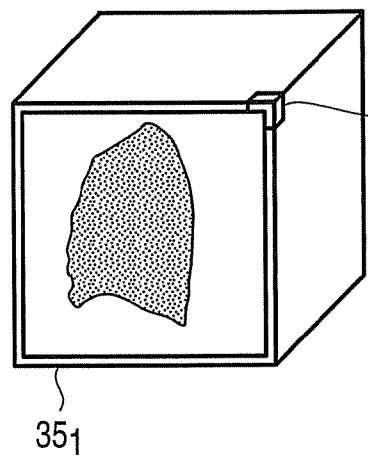 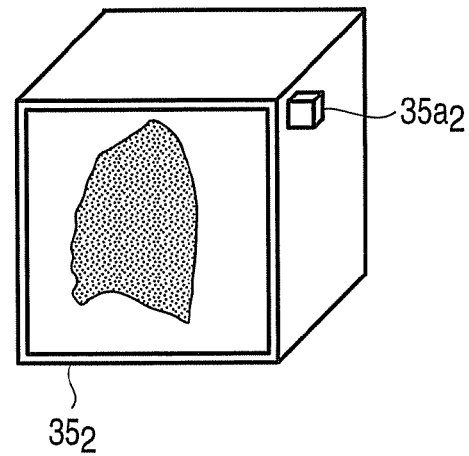
F I G. 4 A			F I G. 4 B
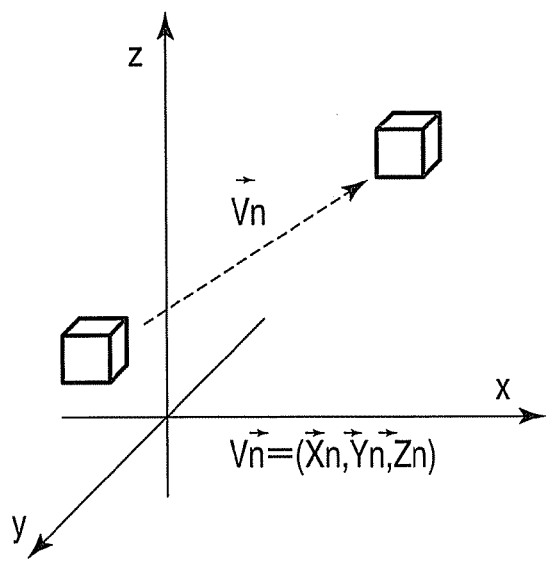
F I G. 4 C

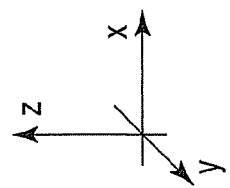
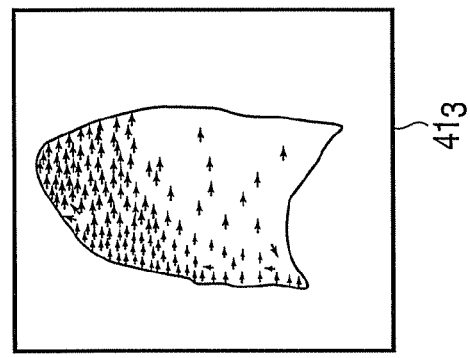
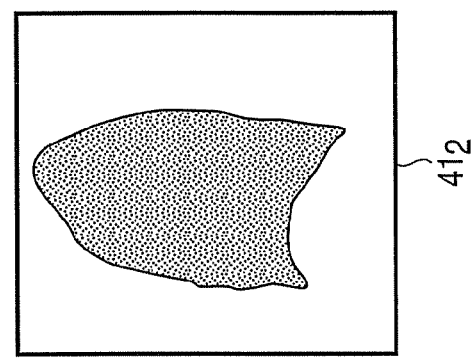
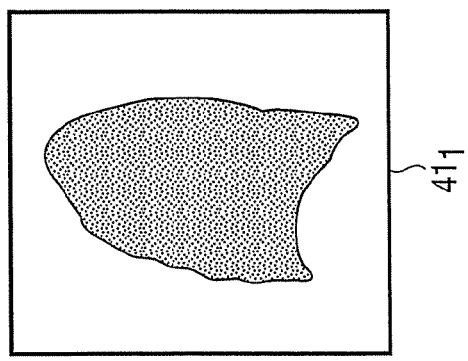
F I G. 7

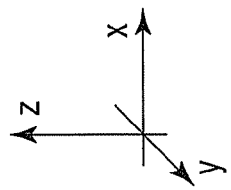
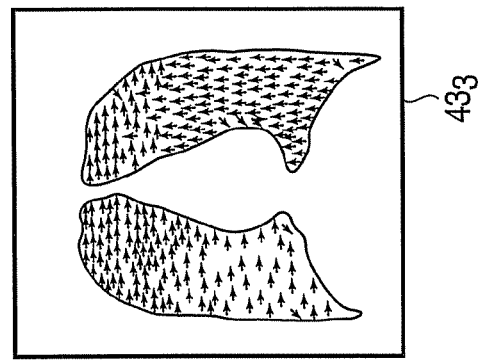
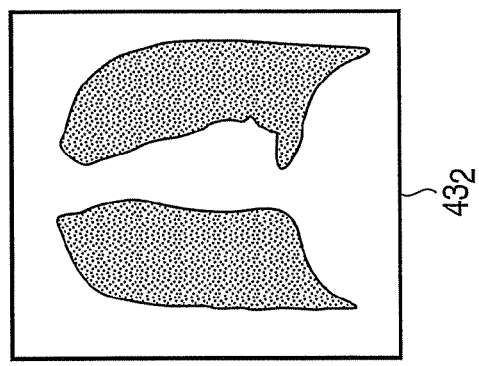
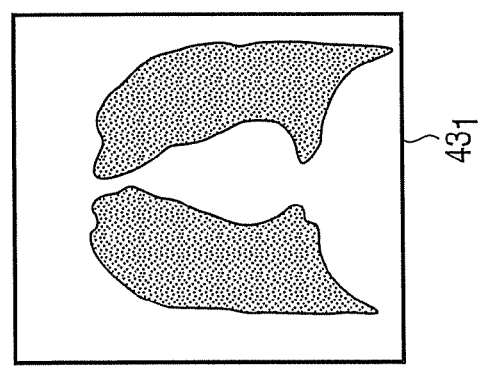
F I G. 8

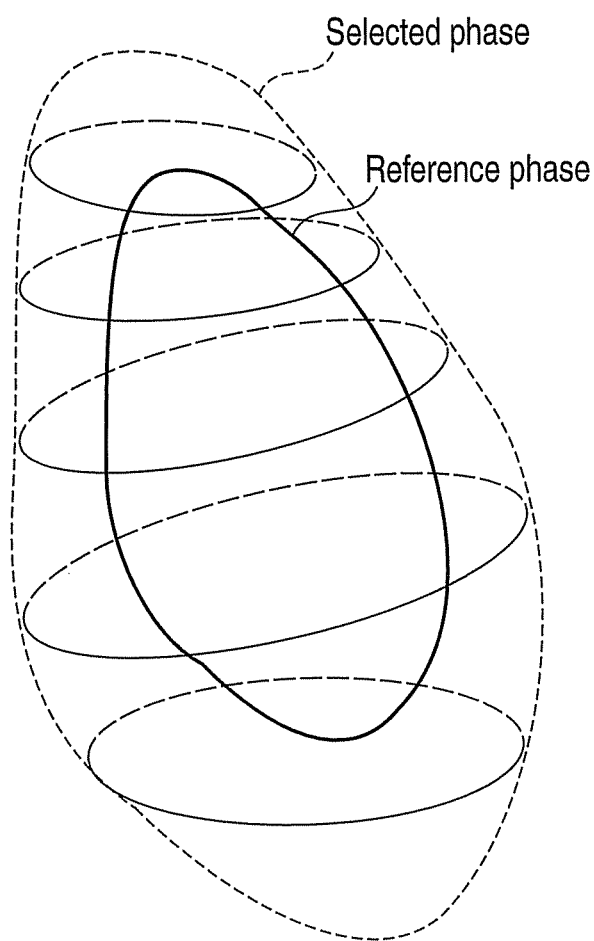
F I G. 10

IMAGE PROCESSING APPARATUS, X-RAY COMPUTED TOMOGRAPHY APPARATUS, AND IMAGE PROCESSING METHOD

CROSS-REFERENCE TO RELATED APPLICATIONS

This application is based upon and claims the benefit of priority from Japanese Patent Application No. 2010-006110, filed Jan. 14, 2010; the entire contents of which are incorporated herein by reference.

FIELD

Embodiments described herein relate generally to an image processing apparatus, an X-ray computed tomography apparatus, and an image processing method.

BACKGROUND

Embodiments described herein relate generally to an image processing apparatus, an X-ray computed tomography apparatus, and an image processing apparatus and, more particularly, to an image processing apparatus, an X-ray computed tomography apparatus, and an image processing method for organ kinetics using medical images, which obtain motion components between phases from data obtained with time using an X-ray computed tomography apparatus (X-ray CT apparatus), a magnetic resonance imaging apparatus (MRI apparatus), or the like and observe the result.

A method of acquiring, for example, image data of a plurality of respiratory phases in the lung field and confirming the tissue kinetics using an X-ray computed tomography apparatus (X-ray CT apparatus), a magnetic resonance imaging apparatus (MRI apparatus), or the like so as to analyze functions is very effective from the viewpoint of disease diagnosis and early disease finding. The function analysis result is also effective from the viewpoint of automated diagnosis (CAD).

The above-described method of grasping kinetics and calculating quantitative values is practiced in general and has received a great deal of attention for a current apparatus such as a CT or MRI capable of time-serially scanning a wide area.

The conventional result observation methods also include a method of evaluating a color map, multi planar reconstruction (MPR) image, or three-dimensional (3D) image as a moving image.

However, the above-described color map is data created based on entire time information, and information at each timing is lost at the time of display. A moving image of MPR or 3D image is hard to grasp the motion of each part of the object.

The embodiments have been made in consideration of the above-described situation, and has as its object to provide an image processing apparatus, an X-ray computed tomography apparatus, and an image processing method for organ kinetics using medical images, which can easily grasp the motion of each part.

BRIEF DESCRIPTION OF THE DRAWINGS

FIG. 1 is a block diagram showing the arrangement of an X-ray computed tomography apparatus according to an embodiment;

FIGS. 4A, 4B, and 4C are views for explaining a motion vector calculation method;

FIG. 7 is a view showing an example of a vector field image generated and displayed in step S5$a$;

FIG. 8 is a view showing an example of a vector field image generated and displayed in step S5$a$;

FIG. 10 is a view showing an example of a wire frame image generated and displayed in step S5$b$.

DETAILED DESCRIPTION

Figure 2:
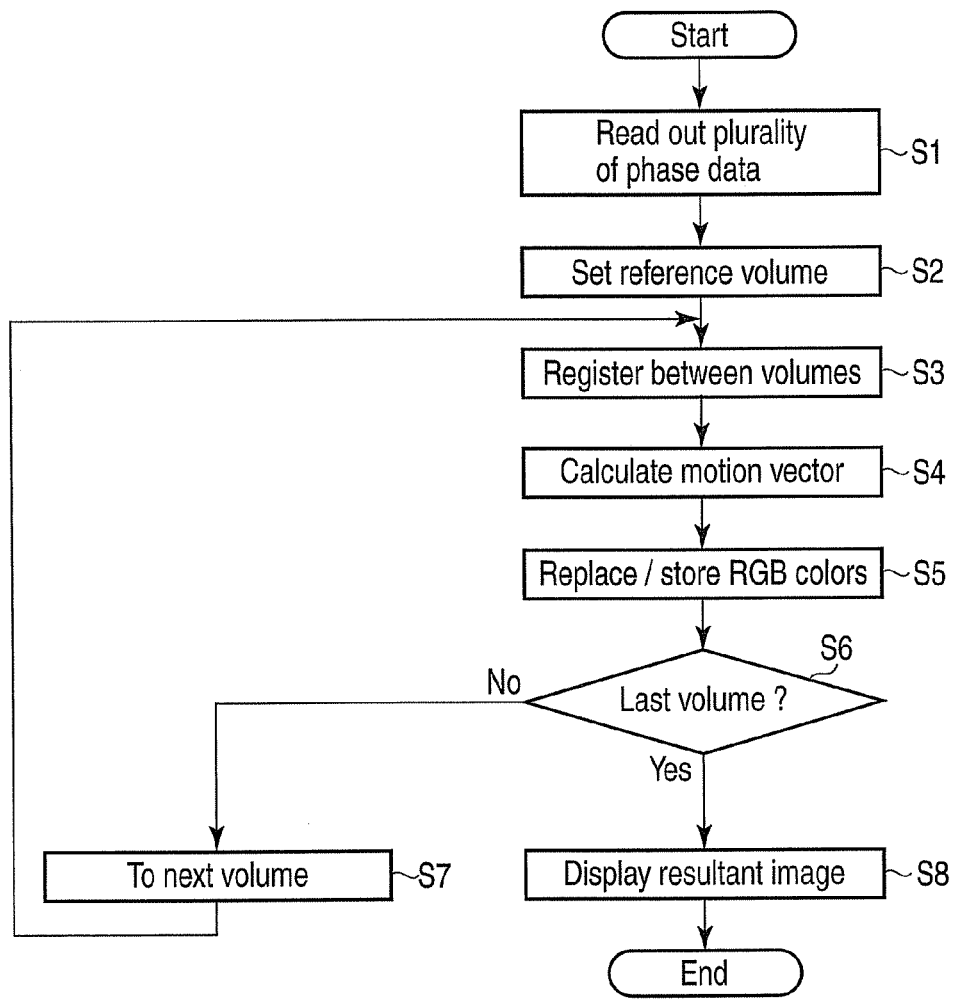
FIG. 2 is a flowchart for explaining an operation of processing an angiographic image obtained by an X-ray CT apparatus 1 in FIG. 1.

In general, according to one embodiment, an image processing apparatus comprises a storage unit configured to store a plurality of volume data acquired by imaging a predetermined part of an object, the plurality of volume data corresponding to a plurality of phases, a calculation unit configured to calculate a spatial motion vector of each voxel included in each volume data by performing registration between the plurality of volume data, an image generation unit configured to generate an image representing a local motion of the diagnosis part using the motion vector of each voxel, and a display unit configured to display the image representing the local motion of the diagnosis part.

The embodiments will now be described with reference to the accompanying drawing. Note that an X-ray computed tomography apparatus will be exemplified in the following embodiments. However, the embodiments are not limited to this example and embodiments related to another medical image diagnostic apparatus (for example, magnetic resonance imaging apparatus, ultrasonic diagnostic apparatus, X-ray diagnostic apparatus, or nuclear medicine diagnostic apparatus) or an image processing apparatus using medical images acquired by the medical image diagnostic apparatus can also be implemented.

FIG. 1 is a block diagram showing the arrangement of an X-ray computed tomography apparatus according to an embodiment.

Note that an X-ray computed tomography apparatus 1 uses either the rotate-rotate method of integrally rotating the X-ray tube and the X-ray detector about an object or the fix-rotate method of rotating only the X-ray tube about an object while arranging a number of X-ray detectors on a ring. The embodiment is applicable to either method. Apparatuses using the rotate-rotate method include an apparatus of single-tube type having a pair of an X-ray tube and an X-ray detector mounted on a rotary frame and an apparatus of multi-tube type having a plurality of pairs of an X-ray tube and an X-ray detector mounted on a rotary frame. The embodiment is applicable to either type. X-ray detectors include a detector of indirect conversion type which causes a phosphor such as a scintillator to convert X-rays transmitted through an object into light and then causes a photoelectric conversion element such as a photodiode to convert the light into electric charges and a detector of direct conversion type which uses electron-hole pair generation in a semiconductor by X-rays and their movement to an electrode, that is, photoconduction. The embodiment is applicable to either type.

Referring to FIG. 1, a gantry 10 includes an X-ray tube 11. The X-ray tube 11 receives a tube voltage and a filament current from a high-voltage generation device via a slip ring mechanism 18, and generates cone-beam-shaped X-rays. The X-ray tube 11 is mounted on a rotary frame 12 rotatably supported about a rotation axis (Z-axis) together with an X-ray detector 13.

A respiration sensor 17 is provided to detect the respiratory motion of the object. In accordance with the inspection target, the respiration sensor 17 can be replaced with an electrocardiograph or heart beat sensor for detecting the phase of the cardiac motion (heart beat) of the object.

The X-ray detector 13 detects X-rays emitted by the X-ray tube 11 and transmitted through the object. The X-ray detector 13 is of a multi-slice type or two-dimensional array type corresponding to a cone beam. More specifically, the X-ray detector 13 has a plurality of X-ray detection element arrays juxtaposed along the rotation axis. Each X-ray detection element array has a plurality of X-ray detection elements arrayed in line along the direction perpendicular to a rotation axis RA.

The output from the X-ray detector 13 is amplified by a data acquisition circuit (DAS) 14 for each channel and converted into a digital signal. The signal is sent to a preprocessing device 16 via, for example, a noncontact data transmitting device 15 and undergoes correction processing such as sensitivity correction. The data is stored in a projection data/image data storage unit 23 as so-called projection data in the stage immediately before reconstruction processing together with a respiratory phase code corresponding to the time the data has been acquired. A scan controller 20 controls a rotation driving unit, a high-voltage generation device 19, the data acquisition circuit 14, the projection data/image data storage unit 23, and the like for data acquisition (scan).

A reconstruction unit 24 reconstructs a plurality of two- or three-dimensional image data in different respiratory phases based on projection data repetitively acquired by dynamic scan. The plurality of two- or three-dimensional image data in different respiratory phases are stored in the projection data/image data storage unit 23 together with a respiratory phase code corresponding to, for example, the center phase of the projection data set used for the reconstruction processing.

A typical three-dimensional image reconstruction processing method is the Feldkamp method. As is known, the Feldkamp method is an approximate reconstruction method based on the fan-beam convolution back projection method. Assuming that the cone angle is relatively small, convolution processing is performed by regarding data as fan projection data. However, the back projection processing is performed along an actual ray. More specifically, a weight depending on the Z-coordinate is assigned to projection data. The same reconstruction function as in fan beam reconstruction is convoluted to the weighted projection data. The data is then reversely projected along an actual oblique ray having a cone angle. The image is reconstructed in accordance with the above-described procedure.

As described above, the X-ray CT apparatus 1 according to this embodiment includes an image processing apparatus. The image processing apparatus comprises a specific phase determination unit 25, display processing unit 26, reference point determination unit 27, point-of-interest determination unit 28, vector processing unit 29, pulmonary function index calculation unit 30, and image processing unit 31 as well as the projection data/image data storage unit 23.

The specific phase determination unit 25 determines the maximum inspiratory phase and the maximum expiratory phase by specifying, for example, the maximum and minimum points of the flow-time curve stored together with the projection data. The reference point determination unit 27 sets a reference point at the same anatomical position on the image of maximum inspiratory phase and the image of maximum expiratory phase. The reference point determination unit 27 also has a function of setting data serving as a reference for registration.

The point-of-interest determination unit 28 sets a plurality of points of interest in, for example, the lung field (for example, the pleura, the bronchium, the bronchiole and the other the lung tissues). A pulmonary function index is obtained from, for example, the moving distance of each point of interest with respect to the reference point in respiration. The plurality of points of interest are set for each of the image of maximum inspiratory phase and the image of maximum expiratory phase. The plurality of points of interest are set on the lung wall contours, nodes, and tumors. The point-of-interest determination unit 28 extracts a lung region from each of the image of maximum inspiratory phase and the image of maximum expiratory phase by threshold processing such as region growing. A point of interest is set on the wall contour of the extracted lung region at each predetermined angle from the reference point.

The vector processing unit 29 calculates a vector for each of the plurality of points of interest on the image of maximum inspiratory phase. Similarly, the vector processing unit 29 also calculates a vector for each of the plurality of points of interest on the image of maximum expiratory phase. The vector processing unit 29 also calculates the vector differences between the plurality of vectors concerning the plurality of points of interest on the image of maximum inspiratory phase and the plurality of vectors concerning the plurality of points of interest on the image of maximum expiratory phase for the respective angles. That is, the moving distance of each point of interest upon respiratory motion is quantitatively obtained based on the relatively stationary reference point. The vector processing unit 29 also has a function of calculating a three-dimensional motion vector ($\vec{x}$, $\vec{y}$, $\vec{z}$) in each voxel based on the deformation amount in nonlinear registration.

The pulmonary function index calculation unit 30 calculates pulmonary function indices such as the quantitative value of the lung volume in each phase, the lung volume change rate, and the quantitative value of each changed volume from the moving distance of each of the plurality of points of interest in calculated respiratory motion. The display processing unit 26 performs processing necessary for displaying the calculated pulmonary function indices as numerical values together with images or in association with a hue or luminance corresponding to each index value at a corresponding position of an image, and displays the pulmonary function indices.

The image processing unit 31 processes various kinds of images such as a medical image and a part model. Although not illustrated, the image processing unit 31 is formed from software or hardware (circuit) or both of them and has a function of registering images and models. The image processing unit 31 also has a function of normalizing the motion vector components calculated by the vector processing unit 29 and assigning them to the (R,G,B) colors, and a function of performing nonlinear registration for data serving as a reference.

An operation of processing an angiographic image will be described next with reference to the flowchart of FIG. 2.

Figure 3:
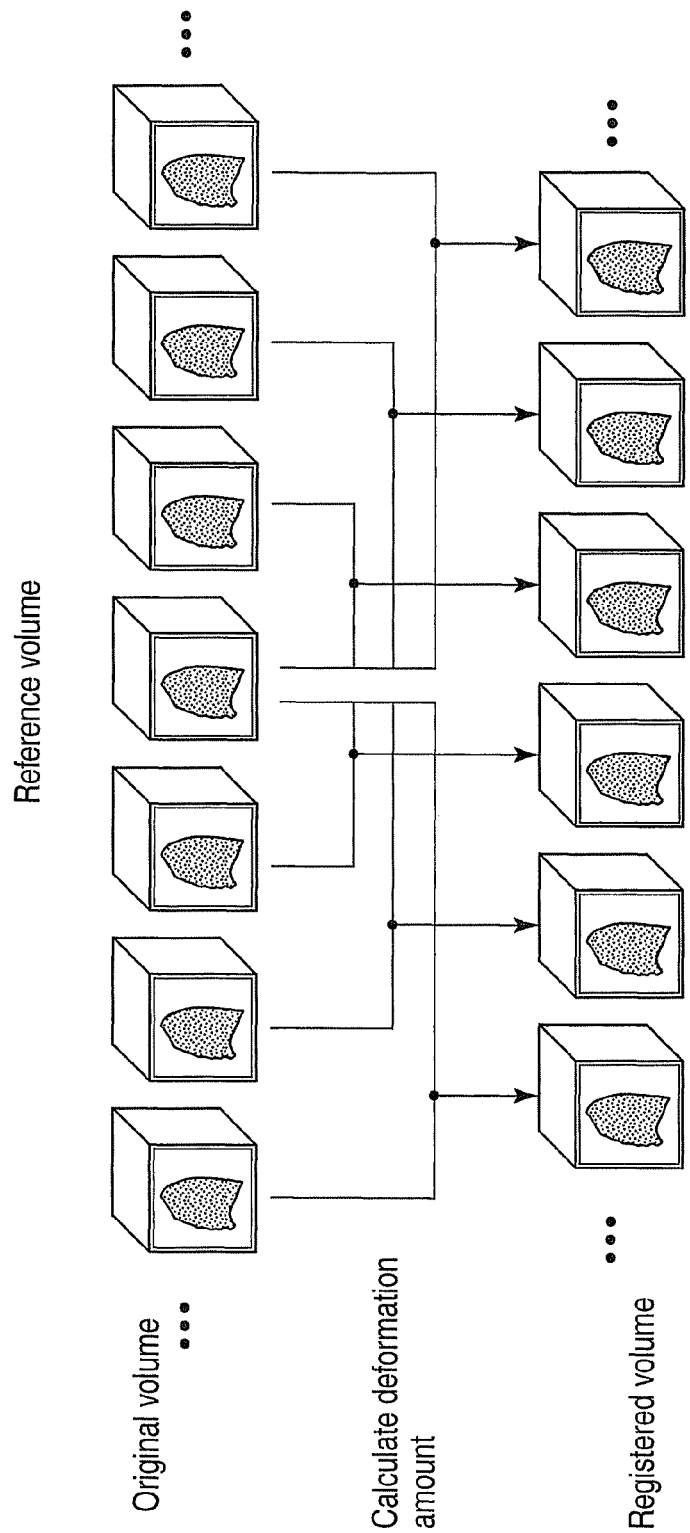
FIG. 3 is a view showing the concept of registration using a reference volume.

An angiographic image obtained using the X-ray CT apparatus 1 shown in FIG. 1 is read out. Note that the readout data has at least two phases. In step S2, a volume serving as a reference for registration is selected from the data read out in step S1. The volume may manually be selected by the operator. Alternatively, a method of automatically detecting a volume with least motion based on the motion difference between phases may be used (FIG. 3). Note that the phase corresponding to the reference volume will be referred to as a "reference phase" hereinafter.

In step S3, registration processing is performed for each phase based on the reference volume set in step S2. Registration between the phases is done using known linear registration or nonlinear registration (for example, Jpn. Pat. Appln. KOKAI Publication No. 2009-28362, and Shinobu Mizuta et al., "Automated, Non-linear Registration Between 3-Dimensional Brain Map and Medical Head Volume", Medical Imaging Technology vol. 16, No. 3, 1998). Hence, a detailed description of these methods will be omitted.

In step S4, the vector processing unit 29 calculates a motion vector component $(\vec{x}, \vec{y}, \vec{z})$ in each voxel based on the deformation amount in registration. For example, place focus on the moving amount of a voxel $35a_1$ between a voxel $35_1$ shown in FIG. 4A and a voxel $35_2$ shown in FIG. 4B after the elapse of a predetermined time. For a moving amount $\vec{V}_n$ from the voxel $35a_1$ to a voxel $35a_2$, a motion vector component $\vec{V}_n = (\vec{x}_n, \vec{y}_n, \vec{z}_n)$ as shown in FIG. 4C is calculated.

In step S5, the motion vector component of each voxel obtained in step S4 is normalized. The image processing unit 31 assigns the (R,G,B) colors to the three-dimensional x- y-, and z-axes (that is, assigns different colors in accordance with the directions and also assigns luminance values corresponding to the magnitudes of the components). The assigned image is stored as a new volume For assignment to (R,G,B), the absolute values $(|\vec{x}|, |\vec{y}|, |\vec{z}|)$ may be calculated, or signed values may directly be assigned. For the signed values, the intermediate value between the minimum value and the maximum value of the vector $(\vec{x}, \vec{y}, \vec{z})$ corresponds to the intermediate value in (R,G,B).

In step S6, the processing operation in steps S3 to S5 described above is performed for all volumes, and for other than the last volume, the process advances to step S7 to shift to the next volume. The process then returns to step S3 to perform registration. Volumes in which the motion vector components are converted into RGB are thus generated.

Finally, in step S8, an MPR image is generated using the volumes obtained in steps S3 to S6 described above, and displayed. The image may be displayed in one phase or as a moving image.

Figures 5A, 5B:
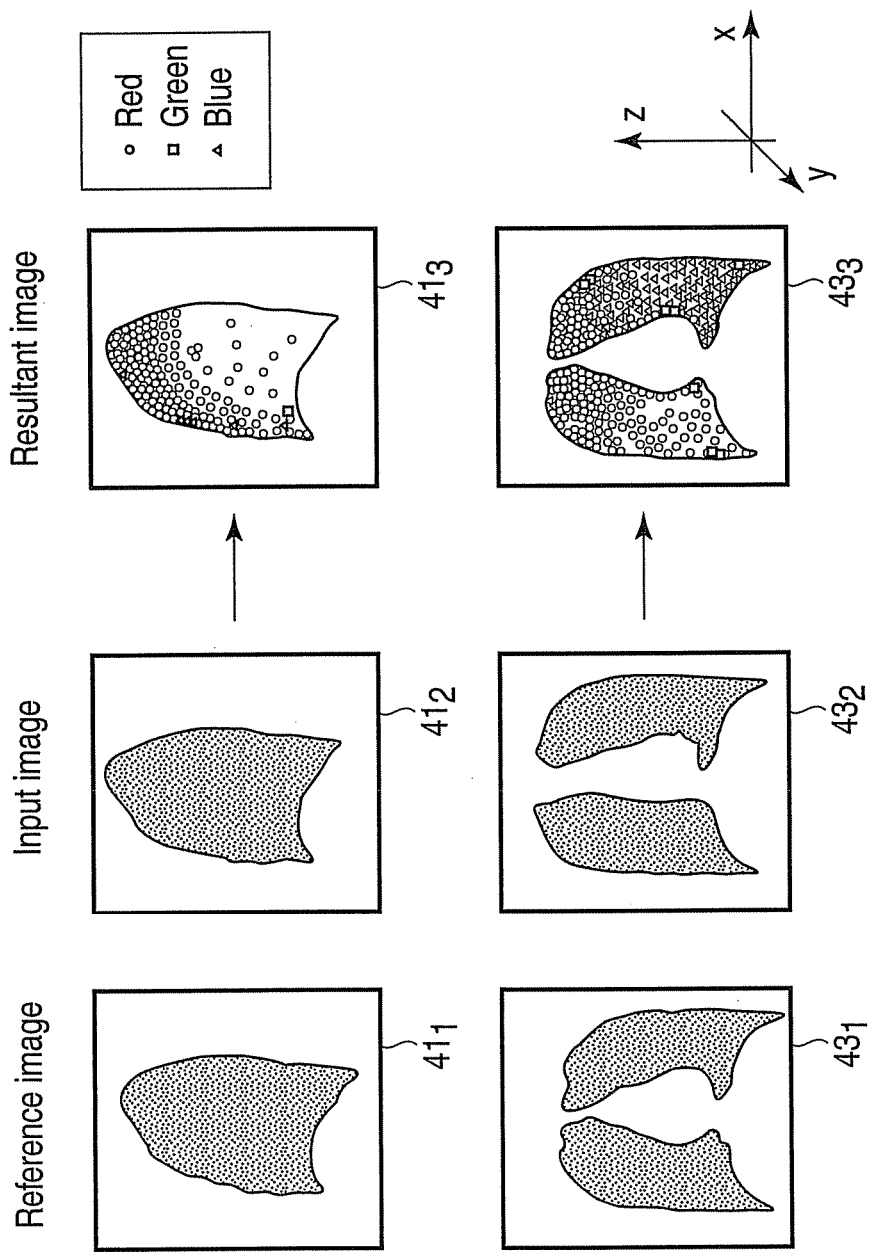
FIGS. 5A and 5B are views showing examples of resultant images.

FIGS. 5A and 5B are views showing examples of images processed by the X-ray CT apparatus 1 according to this embodiment. Note that in FIGS. 5A and 5B, the R component is indicated by ○, the G component is indicated by □, and the B component is indicated by Δ for the convenience. A portion where the components are dense represents that the color of the components is strong (dark). A portion where the components are sparse represents that the color of the components is weak (light).

For example, when an input image $41_2$ is combined with a lung reference image $41_1$ shown in FIG. 5A, a resultant image $41_3$ includes the R components in a large amount as a whole, as can be seen. That is, since the R component corresponds to the x-axis direction, it is determined based on the resultant image $41_3$ that the upper side of the lung mainly moves in the x-axis direction.

In addition, when an input image $43_2$ is combined with a lung reference image $43_1$ shown in FIG. 5B, a resultant image $43_3$ includes the R components in a large amount as a whole, whereas the B components are displayed in a slightly larger amount on the lower right side, as can be seen. That is, it is determined that although the lung moves in the x-axis direction (R component) as a whole, the lower right side moves in the z-axis direction (B component).

As described above, the motion of a three-dimensional image is assigned to the (R,G,B) colors, and the motion vector components are assigned to the directions so as to be displayed as the R, G, and B components. This allows to easily grasp the motion of each part of the object.

For example, a cancer part hardly moves. For this reason, when the (R,G,B) colors are assigned in the above-described manner, a cancer part is supposedly displayed relatively dark so as to be distinguishable from other parts.

Second Embodiment

The second embodiment will be described next. In this embodiment, a local motion of a diagnosis part is indicated as a vector field (vector field indication) using arrows at the respective positions.

Figure 6:
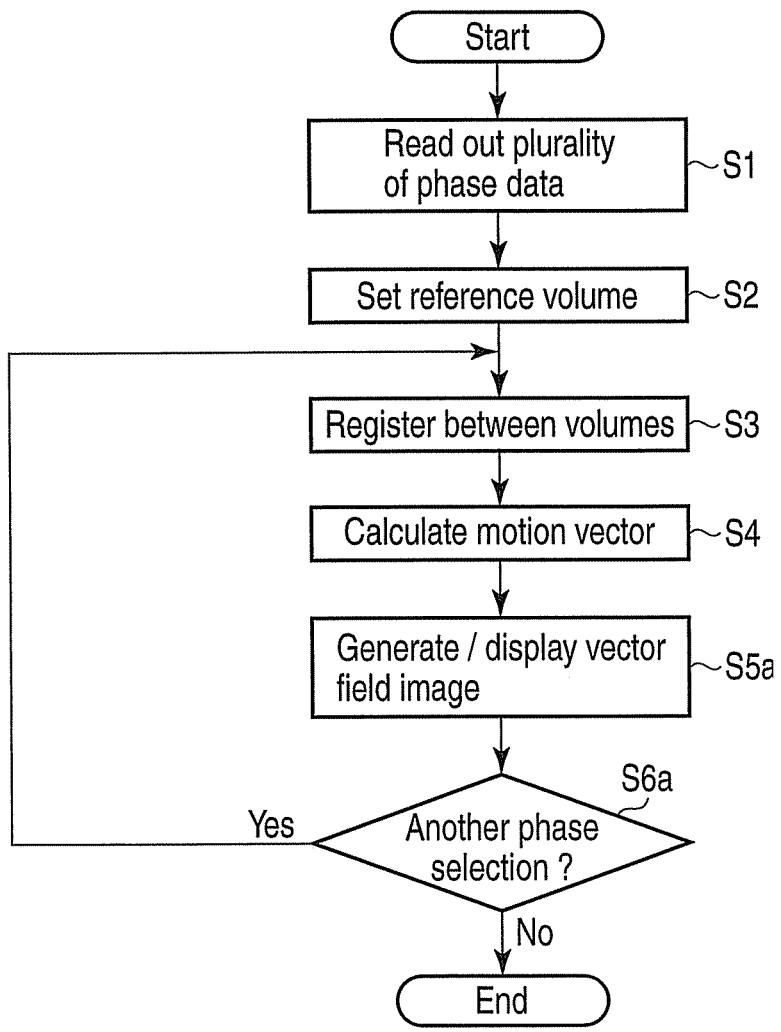
FIG. 6 is a flowchart illustrating the procedure of motion information visualization processing according to the second embodiment.

FIG. 6 is a flowchart illustrating the procedure of motion information visualization processing according to the second embodiment. Processing in steps S1 to S4 is the same as that of the first embodiment shown in FIG. 2. Processing in steps S5a and S6a will be described below.

Using the calculated motion vector of each voxel in each phase, an image processing unit 31 generates an image representing the local motion of a diagnosis part corresponding to a preselected phase (selected phase). More specifically, the image processing unit 31 sets a predetermined MPR section on the volume data of the selected phase. Using the calculated motion vector of each voxel in the selected phase, the image processing unit 31 generates a vector field image which indicates, by arrows, the moving directions and moving amounts at the respective positions on the MPR section. A display processing unit 26 displays the generated vector field image corresponding to the selected phase in a predetermined form (step S5a).

FIGS. 7 and 8 are views showing examples of the vector field image generated and displayed in step S5a. As shown in FIGS. 7 and 8, if a motion has occurred during the period from the reference phase to the selected phase at each position of the MPR image, the moving direction is represented by the direction of the arrow, and the moving amount is represented by the length of the arrow. If no motion has occurred, no arrow representing the moving direction and moving amount is assigned. Hence, the user can easily grasp the motion of the diagnosis part of the object at each position by observing the displayed vector field image.

When an instruction to generate the vector field image of another phase (instruction to select another phase) is input, processing in steps S3 to S5a is repetitively executed for each newly selected phase. If no instruction to select another phase is input, the motion information visualization processing ends (step S6a).

Third Embodiment

The third embodiment will be described next. In this embodiment, a local motion of a diagnosis part is indicated by a wire frame, surface model, or the like.

Figure 9:
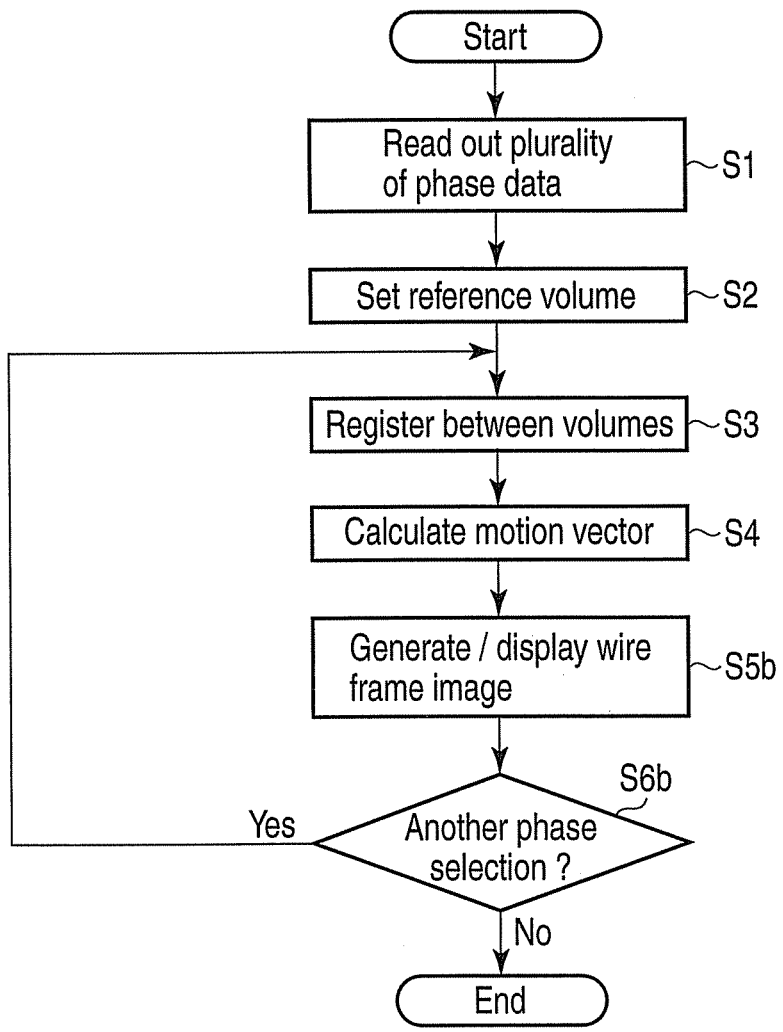
FIG. 9 is a flowchart illustrating the procedure of motion information visualization processing according to the third embodiment.

FIG. 9 is a flowchart illustrating the procedure of motion information visualization processing according to the third embodiment. Processing in steps S1 to S4 is the same as that of the first embodiment shown in FIG. 2. Processing in steps S5b and S6b will be described below.

An image processing unit 31 generates a wire frame image representing the contour of the diagnosis part by a wire frame (or a surface model image representing the surface of the diagnosis part) using the reference volume. Similarly, the image processing unit 31 generates a wire frame image representing the contour of the diagnosis part by a wire frame (or a surface model image representing the surface of the diagnosis part) using a volume corresponding to a preselected phase (selected phase). The image processing unit 31 also generates an image representing the local motion of the diagnosis part using the generated wire frame images and the motion vector of each voxel during the period from the reference phase to the selected phase. That is, the image processing unit 31 registers the wire frame corresponding to the reference phase with the wire frame corresponding to the selected phase and also adds information representing a motion to the wire frame corresponding to the selected phase, thereby generating the image representing the local motion of the diagnosis part. A display processing unit 26 displays the generated wire frame image corresponding to the selected phase in a predetermined form (step S5b).

Note that the information representing the motion and to be added to the wire frame corresponding to the selected phase can be of any type. For example, (R,G,B) assignment described in the first embodiment may be performed at each position on the wire frame. Alternatively, vector field indication described in the second embodiment may be performed at each position on the wire frame. Not motion at each position but an average motion magnitude and motion direction within a predetermined range may be indicated by an arrow or the like.

FIG. 10 is a view showing an example of a wire frame image generated and displayed in step S5b. As shown in FIG. 10, the user can easily and quickly visually recognize the motion at each position the contour during the period from the reference phase to the selected phase by observing the wire frame image.

When an instruction to generate the wire frame image of another phase (instruction to select another phase) is input, processing in steps S3 to S5b is repetitively executed for each newly selected phase. If no instruction to select another phase is input, the motion information visualization processing ends (step S6b).

In the above-described embodiments, one resultant image is displayed for each part. However, the embodiments are not limited to this. For example, the images may be overlaid. In the embodiments, a still image has been exemplified. However, the embodiments are not limited to this and are also applicable to a moving image.

In the embodiments, the reference volume is set in step S2. Registration with the reference volume is done to calculate the motion vector of each voxel from the phase corresponding to the reference volume. However, the embodiments are not limited to this example. For example, registration may be done between chronologically adjacent volumes to calculate the motion vector of each voxel between the phases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a storage unit configured to store a plurality of volume data acquired by imaging a predetermined part of an object, the plurality of volume data corresponding to a plurality of phases;
a calculation unit configured to calculate a motion vector of each voxel included in each volume data by performing registration between the plurality of volume data; an image generation unit configured to generate an image representing a local motion of a diagnosis part using the motion vector of each voxel, the local motion of the diagnosis part being indicated in a predetermined set of direction components of the motion vector, one of predetermined different colors and luminances being assigned to a corresponding one of the direction components in accordance with a magnitude of the corresponding one of the direction components; and
a display unit configured to display the image representing the local motion of the diagnosis part.

2. The apparatus according to claim 1, wherein the calculation unit calculates the motion vector by performing registration based on predetermined volume data selected from the plurality of volume data.

3. The apparatus according to claim 1, wherein the calculation unit calculates the motion vector by performing registration between chronologically adjacent volumes.

4. The apparatus according to claim 1, wherein the calculation unit normalizes the motion vector.

5. The apparatus according to claim 1, wherein the image generation unit generates the image representing the local motion of the diagnosis part by assigning the components of the motion vector to (R,G,B).

6. The apparatus according to claim 1, wherein the image generation unit generates the image representing the local motion of the diagnosis part by indicating each motion vector by an arrow at each spatial position.

7. The apparatus according to claim 1, wherein the image generation unit generates the image representing the local motion of the diagnosis part by visualizing a contour of the predetermined part in a first phase and a contour of the predetermined part in a second phase after elapse of a predetermined time from the first phase.

8. The apparatus according to claim 1, wherein the image generation unit generates the image representing the local motion of the diagnosis part as an MPR image.

9. The image processing apparatus according to claim 1, wherein the predetermined part of the object includes at least one of a pleura, a bronchium and a bronchiole.

10. An X-ray computed tomography apparatus comprising:
an imaging unit configured to image volume data concerning a predetermined part of an object in a plurality of phases;
a calculation unit configured to calculate a spatial motion vector between the phases for each voxel included in each volume data by performing registration between the plurality of volume data;
an image generation unit configured to generate an image representing a local motion of a diagnosis part using the motion vector of each voxel, the local motion of the diagnosis part being indicated in a predetermined set of direction components of the motion vector, one of predetermined different colors and luminances being assigned to a corresponding one of the direction components in accordance with a magnitude of the corresponding one of the direction components; and a display unit configured to display the image representing the local motion of the diagnosis part.

11. The apparatus according to claim 10, wherein the calculation unit calculates the motion vector by performing registration based on predetermined volume data selected from the plurality of volume data.

12. The apparatus according to claim 10, wherein the calculation unit calculates the motion vector by performing registration between chronologically adjacent volumes.

13. The apparatus according to claim 10, wherein the calculation unit normalizes the motion vector.

14. The apparatus according to claim 10, wherein the image generation unit generates the image representing the local motion of the diagnosis part by assigning the components of the motion vector to (R,G,B).

15. The apparatus according to claim 10, wherein the image generation unit generates the image representing the local motion of the diagnosis part by indicating each motion vector by an arrow at each spatial position.

16. The apparatus according to claim 10, wherein the image generation unit generates the image representing the local motion of the diagnosis part by visualizing a contour of the predetermined part in a first phase and a contour of the predetermined part in a second phase after elapse of a predetermined time from the first phase.

17. The apparatus according to claim 10, wherein the image generation unit generates the image representing the local motion of the diagnosis part as an MPR image.

18. An image processing method comprising:

executing registration between a plurality of volume data acquired by imaging a predetermined part of an object using an image processing apparatus, the plurality of volume data corresponding to a plurality of phases;

calculating a spatial motion vector between the phases for each voxel included in each volume data;

generating an image representing a local motion of a diagnosis part using the motion vector of each voxel, the local motion of the diagnosis part being indicated in a predetermined set of direction components of the motion vector, one of predetermined different colors and luminances being assigned to a corresponding one of the direction components in accordance with a magnitude of the corresponding one of the direction components; and displaying the image representing the local motion of the diagnosis part.

* * * * *